United States Patent [19]

Tofe et al.

[11] 3,965,254

[45] June 22, 1976

[54] COMPOSITIONS FOR THE TREATMENT OF CALCIFIC TUMORS

[75] Inventors: Andrew John Tofe; Marion David Francis, both of Cincinnati, Ohio

[73] Assignee: The Procter & Gamble Company, Cincinnati, Ohio

[22] Filed: Nov. 15, 1974

[21] Appl. No.: 524,013

Related U.S. Application Data

[63] Continuation-in-part of Ser. No. 362,971, May 23, 1973.

[52] U.S. Cl. .............................. 424/1; 260/502.4 P; 260/502.4 R; 260/502.5
[51] Int. Cl.² .................... A61K 43/00; C07F 9/02
[58] Field of Search ............... 260/502.4 P, 502.4 R, 260/502.5; 424/1

[56] References Cited
UNITED STATES PATENTS

| | | | |
|---|---|---|---|
| 3,213,129 | 10/1965 | Berth et al. | 260/502.4 X |
| 3,336,221 | 8/1967 | Ralston | 260/502.5 X |
| 3,387,024 | 6/1968 | Quimby | 260/502.4 |
| 3,400,151 | 9/1968 | Quimby et al. | 260/502.4 |
| 3,532,639 | 10/1970 | Hatch | 260/502.4 |
| 3,553,314 | 1/1971 | Francis | 260/502.4 X |
| 3,553,315 | 1/1971 | Francis | 260/502.4 X |
| 3,579,570 | 5/1971 | Nicholson et al. | 260/502.4 X |
| 3,743,688 | 7/1973 | Nicholson et al. | 260/502.4 X |

*Primary Examiner*—Benjamin R. Padgett
*Assistant Examiner*—Christine M. Nucker

[57] ABSTRACT

Composition in unit dosage form comprising mono-, di- and polyphosphonate compounds having therapeutic levels of radioactive phosphorus (as $^{32}P$ and $^{33}P$) incorporated therein are disclosed. Due to the extremely high affinity of the polyphosphonate compounds for active bone tumors and their exceptionally low retention in soft tissue they are ideal for therapy of both primary and metastatic bone tumors and soft tissue tumors which calcify.

15 Claims, No Drawings

COMPOSITIONS FOR THE TREATMENT OF CALCIFIC TUMORS

RELATED APPLICATIONS

This application is a continuation-in-part of application Ser. No. 362,971, filed May 23, 1973.

BACKGROUND OF THE INVENTION

This invention relates to radiopharmaceuticals and more particularly to such materials suited for use in treatment of calcific tumors; i.e., primary and metastatic bone tumors and soft tissue calcifying tumors.

Radiation therapy for tumors of various types has been well known for some time. One of the main difficulties with all radiation therapy is the lack of specificity of both externally applied radiation and radioactive materials; i.e., the radiation therefrom is generalized and has a substantial effect on bone marrow activity and soft tissue which is not tumerous as well as that which is.

Attempts have been made heretofore to provide site selective radiopharmaceuticals with some success. For example Storaasli reported in the Journal of the American Medical Association 210, 1077–1078 (1969) that sodium phosphate having incorporated therein the radioactive isotope of phosphorus having an atomic weight of 32 ($^{32}P$) had a measure of selectivity for osseous tumors. The selectivity achieved by this approach is apparently related to the high uptake of phosphorus in tumors as reported by Anghileri in Experientia 28 Number 9, 1086–7 (1972) but is insufficient to allow an effective dose of radioactivity to be directed to a bone tumor without simultaneously directing a damaging dose to unaffected bone, bone marrow and other soft tissue cells. Consequently radioactive phosphates (and polyphosphates) have been restricted to use in extreme or terminal bone tumor cases where the high risks of additional damage were warranted.

Prior to the present invention, no compound or method existed whereby effective therapeutic or pain relieving doses of radiation could be directed to bone tumor sites without a substantial risk of radiation damage to the remainder of the body.

Accordingly, it is the object of this invention to provide a means for introducing quantities of radiation sufficient to reduce pain and/or have a therapeutic effect on primary or metastatic tumors without simultaneously damaging non-tumorous bone, bone marrow and soft tissue and cells.

SUMMARY OF THE INVENTION

It has now been discovered that the above object can be achieved by providing compositions in unit dosage form comprising mono-, di- and polyphosphates having incorporated therein a radiouclide selected from the group $^{32}P$ and $^{33}P$. In its method aspects, the present invention comprises systemically administering effective amounts of such compounds to an animal afflicted with a calcific tumor.

DESCRIPTION OF THE PREFERRED EMBODIMENTS

A host of mono-, di- and polyphosphonates have recently been found to exhibit generalized attraction to osseous sites and are useful in inhibiting the anomalous deposition and mobilization of calcium phosphate in animal tissue as disclosed in U.S. Pat. No. 3,683,080 which issued Aug. 8, 1972, to M. D. Francis. It has now been discovered that certain mono-, di-, and polyphosphonates wherein a radionuclide selected from the group $^{32}P$ and $^{33}P$ is used in place of stable $^{31}P$ exhibit unexpectedly and usefully high selectivity for calcific tumors in addition to the high but generalized calcific selectivity formerly associated therewith.

Such "tagged" or radioactive phosphonates have, as will hereinafter be described, sufficient selectivity for primary and metastatic bone tumors that effective amounts of $^{32}P$ or $^{33}P$ radionuclide can be delivered to the tumor site without adversely affecting non-tumorous sites. Selectively as great as 40:1 has been demonstrated in dogs with proven osteogenic sarcoma; i.e., the tumorous site can contain 40 times as much radioactivity as the corresponding but opposite and unaffected bone (hereinafter referred to as the contralateral bone) or as adjacent normal bone (as in sternum or spine area).

The preferred radioactive phosphonates are those containing the radionuclide $^{33}P$.

Suitable $^{32}P$ and $^{33}P$ containing phosphonates (for simplicity, $^{32}P$ and $^{33}P$ will generally be referred to simply as P in the following list of structural variations) for use with the present inventon include the group consisting of:

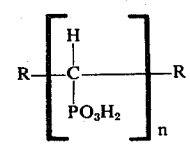

I.

wherein each R is hydrogen or $CH_2OH$ and $n$ is an integer of from 3 to 10;

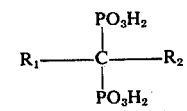

II.

wherein $R_1$ is hydrogen, alkyl containing from 1 to about 20 carbon atoms, alkenyl containing from 2 to about 20 carbon atoms, aryl (e.g., phenyl, naphthyl), phenylethenyl, benzyl, halogen (e.g., chlorine, bromine and fluorine), hydroxyl, amino, substituted amino (e.g., dimethylamino, diethylamino, N-hydroxy-N-ethylamino, acetylamino), $-CH_2COOH$, $-CH_2PO_3H_2$, $-CH(PO_3H_2)(OH)$, $-[CH_2C(PO_3H_2)_2]_nH$ where n is 1 to 15, $R_2$ is hydrogen, lower alkyl (e.g., methyl, ethyl, propyl and butyl), amino, benzyl, halogen (e.g., chlorine, bromine, and fluorine), hydroxyl, $-CH_2COOH$, $-CH_2PO_3H_2$, or $-CH_2CH_2PO_3H_2$;

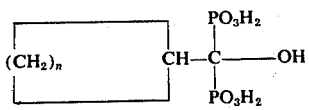

III.

wherein $n$ is an integer of from 3 to 9;

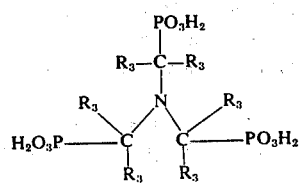

IV.

wherein each $R_3$ is hydrogen or lower alkyl (e.g., methyl, ethyl, propyl and butyl);

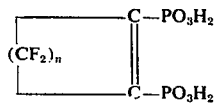    V.

wherein $n$ is an integer of from 2 to 4;

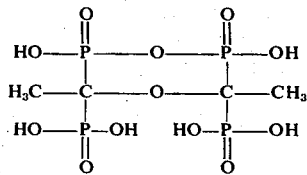    VI.

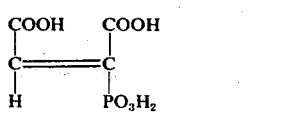    VII.

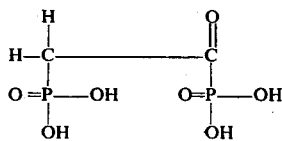    VIII.

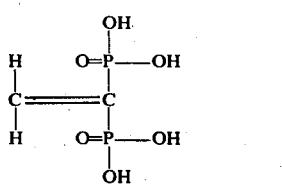    IX.

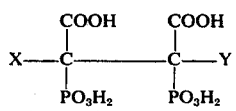    X.

wherein X and Y are hydrogen or hydroxy; and the pharmaceutically acceptable salts of each of the foregoing acids, e.g., alkali metal (sodium and potassium), alkaline earth metal (calcium and magnesium), nontoxic heavy metal (stannous ad indium) and ammonium and low molecular weight substituted ammonium (mono-, di- and triethanolamine) salts.

Operable polyphosphonates of the above formula (I) include propane-1,2,3-triphosphonic acid; butane-1,2,3,4-tetraphosphonic acid; hexane-1,2,3,4,5,6-hexaphosphonic acid; hexane-1-hydroxy -2,3,4,5,6-pentaphosphonic acid; hexane-1,6-dihydroxy-2,3,4,5-tetraphosphonic acid; pentane-1,2,3,4,5-pentaphosphonic acid; hexane-1,2,3,4,5,6-hexaphosphonic acid; heptane-1,2,3,4,5,6,7-heptaphoshonic acid; octane-1,2,3,4,5,-6,7,8-octaphosphonic acid, nonane-1,2,3,4,5,6,7,8,9-nonaphosphonic acid; decane-1,2,3,4,5,6,7,8,9,10-decaphosphonic acid; and the pharmaceutically acceptable salts of these acids, e.g., sodium, potassium, calcium, magnesium, ammonium, triethanolammonium, diethanolammonium, and monoethanolammonium salts.

Phosphorus-32 and phosphorus-33 are commercially available. The materials can be reacted conventionally to form $PCl_3$. $PCl_3$ is a suitable starting material for all of the syntheses herein outlined. $PCl_3$ can be made into suitable intermediates for the disclosed structures by the following reactions:

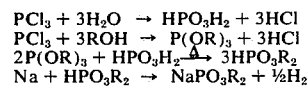

A useful outline of reactions to form polyphosphonates from these materials is found in "Topics in Phorphorous Chemistry" (Chapter 7, "Oligophosphonates", Wiley, 1972).

Propane-1,2,3-triphosphonic acid and salts thereof can be prepared by a process disclosed in the copending application of D. Allan Nicholson and Darrel Campbell, Ser. No. 82,819, filed Oct. 21, 1970, now U.S. Pat. No. 3,743,688.

Butane-1,2,3,4-tetraphosphonic acid and salts thereof can be prepared by a process disclosed in the copending application of D. Allan Nicholson and Darrel Campbell, Ser. No. 67,200, filed Aug. 26, 1970, now U.S. Pat. 3,755,504.

The higher aliphatic vicinal polyphoshonates and salts thereof can be prepared by the process disclosed in U.S. Patent 3,584,035 granted June 8, 1971.

Among the operable polyphosphonates encompassed by the above formula (II) are ethane-1-hydroxy-1,1-diphosphonic acid; methanediphosphonic acid; methanehydroxydiphosphonic acid; ethane-1,1,2-triphosphonic acid; propane-1,1,3,3-tetraphosphonic acid; ethane-2-phenyl-1,1-diphosphonic acid; ethane-2-naphthyl-1,1-diphosphonic acid; methanephenyldiphosphonic acid; ethane-1-amino-1,1-diphosphonic acid; methanedichlorodiphosphonic acid; nonane-5,5-diphosphonic acid; n-pentane-1,1-diphosphonic acid; methanedifluorodiphosphonic acid; propane-2,2-diphosphonic acid; ethane-2-carboxy-1,1-diphosphonic acid; propane-1-hydroxy-1,1,3-triphosphonic acid; ethane-2-hydroxy-1,1,2-triphosphonic acid; ethane-1-hydroxy-1,1,2-triphosphonic acid; propane-1,3-diphenyl-2,2-diphosphonic acid; nonane-1,1-diphosphonic acid; hexadecane-1,1-diphosphonic acid; pent-4-ene-1-hydroxy-1,1-diphosphonic acid; octadec-9-ene-1-hydroxy-1,1-diphosphonic acid; 3-phenyl-1,1-diphosphono-prop-2-ene; octane-1,1-diphosphonic acid; dodecane-1,1-diphosphonic acid; phenylaminomethanediphosphonic acid; naphthylaminomethanediphosphonic acid; N,N-dimethylaminomethanediphosphonic acid; N-(2-dihydroxyethyl)-aminomethanediphosphonic acid; N-acetylaminomethanediphosphonic acid; aminomethanedisphosphonic acid; dihydroxymethanediphosphonic acid; and the pharmaceutically acceptable salts of these acids, e.g., sodium potassium, calcium, magnesium, stannous, indium, ammonium, triethanolammonium, diethanolammonium, and monoethanolammonium salts.

Ethane-1-hydroxy-1,1-diphosphonic acid, an especially preferred polyphosphonate, has the molecular formula $CH_3C(OH)(PO_3H_2)_2$. (According to nomenclature by radicals, the acid might also be named 1-hydroxyethylidene diphosphonic acid.)

While any pharmaceutically acceptable salt of ethane-1-hydroxy-1,1-diphosphonic acid can be used in the practice of this invention, the disodium dihydrogen salt is preferred. The other sodium, potassium, ammonium, and mono-, di-, and triethanolammonium salts and mixtures thereof are also suitable provided caution is observed in regulating the total intake of cation species in the salt composition. These compounds can be prepared by any suitable method, however, an especially preferred method is disclosed in U.S. Pat. No. 3,400,149 granted Sept. 3, 1968.

Methanehydroxydiphosphonic acid and related compounds operable herein can be prepared, for example, by reaction of phosgene with an alkali metal dialkylphosphite. A complete description of these compounds and a method for preparing same is found in U.S. Pat. No. 3,422,137 granted Jan. 14, 1969.

Methanedihydroxydiphosphonic acid and salts useful herein and a method for preparing same are disclosed in U.S. Pat. No. 3,497,313 granted Feb. 24, 1970.

Methanediphosphonic acid and related compounds useful herein are described in detail in U.S. Pat. No. 2,213,030, granted October 19, 1965. A preferred method of preparing such compounds is disclosed in U.S. Pat. No. 3,251,908, granted May 17, 1966.

Ethane-1,1,2-triphosphonic acid and related compounds which can be used in the compositions of this invention, as well as a method for their preparation, are fully described in U.S. Pat. No. 3,551,339, granted Dec. 29, 1970.

Propane-1,1,3,3-tetraphosphonic acid and related compounds useful herein, and a method for preparing same are fully disclosed in U.S. Pat. No. 3,400,176, granted Sept. 3, 1968. The higher methylene interrupted methylene diphosphonate can be prepared by the polymerization of ethylene-1,1-diphosphonate.

Pentane-2,2-diphosphonic acid and related compounds can be prepared in accordance with the method described by G. M. Kosolopoff in J. Amer. Chem. Soc., 75, 1500 (1953).

Operable phosphonates of formula (III) above include the following:
Methanecyclobutylhydroxydiphosphonic acid
Methanecyclopentylhydroxydiphosphonic acid
Methanecyclohexylhydroxydiphosphonic acid
Methanecycloheptylhydroxydiphosphonic acid
Methanecyclooctylhydroxydiphosphonic acid
Methanecyclononylhydroxydiphosphonic acid
Methanecyclodecylhydroxydiphosphonic acid Each of the sodium, potassium, calcium, magnesium, stannous, indium, ammonium, monoethanolammonium, diethanolammonium and triethanolammonium salts of the above recited methanecycloalkylhydroxydiphosphonic acids as well as any other pharmaceutically acceptable salt of these acids, also selectivity seek the skeleton.

The phosphonates of formula (III) can be prepared by methods fully described in U.S. Pat. No. 3,584,125, granted June 8, 1971.

The preferred phosphonates of formula (IV) for the purpose of this invention are tris(phosphonoemethyl)amine; tris(1-phosphonoethyl)amine; tris(2-phosphono-2-propyl)amine; and their pharmaceutically acceptable salts. Tris(phosphonomethyl)amine is especially preferred. The following are exemplary of compounds which can also be used.

a. bis(phosphonomethyl)-1-phosphonoethyl amine;
b. bis(phosphonomethyl)-2-phosphono-2-propyl amine;
c. bis(1-phosphonoethyl)phosphonomethyl amine;
d. bis(2-phosphono-2-propyl)phosphonomethyl amine;
e. tris(1-phosphono-1-pentyl)amine;
f. bis(phosphonomethyl)2-phosphono-2-hexyl amine; and
g. the pharmaceutically acceptable salts of acids (a) through (f), e.g., sodium, potassium, calcium, magnesium, ammonium, triethanolammonium, diethanolammonium, and monoethanolammonium salts.

The tris(phosphonoalkyl)amines can be prepared, for example, by first preparing the corresponding ester in accordance with the general reaction:

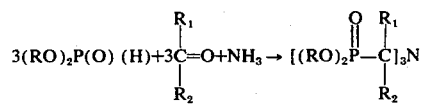

wherein R is alkyl and $R_1$ and $R_2$ are hydrogen or lower alkyl.

The free acids can be prepared by hydrolysis of the ester using strong mineral acids such as hydrochloric acid. The salts are, of course, prepared by neutralizing the acid with the base of the desired cation. The preparation of tris(phosphonalkyl)amines is fully disclosed by Irani, et al., in Canadian Pat. No. 753,207, issued Feb. 21, 1967.

The phosphonates of formula (V) include the following:

1. 3,3,4,4,5,5,-hexafluoro-1,2-diphosphonocyclopent-1-ene;
2. 3,3,4,4-tetrafluoro-1,2-diphosphonocyclobut-1-ene; and
3. 3,3,4,4,5,5,6,6-octafluoro-1,2-diphosphonocyclohex-1-ene.

The perfluorodiphosphonocycloalkenes can be prepared, for example, by reacting trialkyl phosphites with 1,2-dichloroperfluorocycloalk-1-enes in accordance with the procedures fully described by Frank in J. Org. Chem., 31, No. 5, p. 1521.

The phosphonate of formula (VI) is referred to herein as cyclic tetraphosphonic acid. This compound and its pharmaceutically acceptable salts can be prepared by any suitable method, however, an especially preferred method is disclosed by Oscar T. Quimby, U.S. Pat. No. 3,387,024 granted June 4, 1968.

Operable phosphonates encompassed by the above formula (VII) are ethene-1,2-dicarboxy-1-phosphonic acid; and the pharmaceutically acceptable salts of these acids, e.g., sodium, potassium, calcium, magnesium, stannous, indium, ammonium, triethanolammonium diethanolammonium, and monoethanolammonium salts. While the above formula (VII) is representative of cis-isomers, the corresponding trans-isomers are also useful herein. Reference hereinafter to ethene-1,2-dicarboxy-1-phosphonic acid or salts thereof, unless otherwise specified, is intended as contemplating the cis- and trans-isomers and mixtures thereof.

Ethene-1,2-dicarboxy-1-phosphonic acid and related compounds useful herein can be prepared by reacton of an ester of acetylenedicarboxylic acid and a dialkyl phosphite followed by hydrolysis and saponification. This method is more fully described in U.S. Pat. No. 3,584,124, granted June 8, 1971.

Phosphonates of the formula VIII can be made in rearrangement reactions of the type:

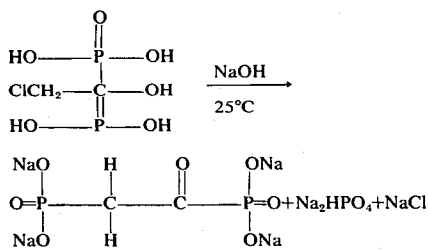

The phosphonates of formula IX can be made by the method of German Offenlegungsschrift No. 2,026,078.

Operable carboxyphosphonates of the above formula (X) include ethane-1,2-dicarboxy-1,2-diphosphonic acid; ethane-1,2-dicarboxy-1,2-dihydroxy-1,2-diphosphonic acid; ethane-1,2-dicarboxy-1-hydroxy-1,2-diphosphonic acid; and the pharmaceutically acceptable salts of these acids, e.g., sodium, potassium, calcium, magnesium, ammonium, triethanolammonium, diethanolammonium and monoethanolammonium salts.

Ethane-1,2-dicarboxy-1,2-diphosphonic acid, a preferred carboxyphosphonate herein, has the molecular formula $CH(COOH)(PO_3H_2)CH(COOH)(PO_3H_2)$. The most conveniently crystallizable salts of this acid are obtained when three, four or five of the acid hydrogens are replaced by sodium.

While any pharmaceutically acceptable salt of ethane-1,2-dicarboxy-1,2-diphosphonic acid can be used in the practice of this invention, the tetrasodium dihydrogen salt, the trisodium trihydrogen salt, the disodium tetrahydrogen salt, the monosodium pentahydrogen salt, and the mixtures thereof are preferred. The other sodium, potassium, ammonium, and mono-, di-, and triethanolammonium salts and mixtures thereof are also suitable.

Ethane-1,2-dicarboxy-1,2-diphosphonic acid and suitable salts thereof can be prepared in any convenient manner. For example, the reaction described by Pudovik in "Soviet Research on Organo-Phosphorus Compounds", 1949–1956, Part III, 547, 85c can be used to prepare the ester of ethane-1,2-dicarboxy-1,2-diphosphonic acid which in turn can, by ordinary hydrolysis reactions, be converted to the free acid form. Neutralization by alkali compounds such as sodium hydroxide, potassium hydroxide, carbonates and the like can be used to prepare a desired salt of the acid. A more detailed description of the preparation of these compounds is described in U.S. Pat. No. 3,562,166 granted Feb. 9, 1971.

Ethane-1,2-dicarboxy-1,2--dihydroxy-1,2-diphosphonic acid and related compounds useful herein can be prepared by reaction of an ester of ethane-1,2-dicarboxy-1,2-diphosphonic acid and an alkali metal hypohalite followed by hydrolysis and saponification. This method is more fully described in U.S. Pat. No. 3,579,570 granted May 18, 1971.

Mixtures of any of the foregoing phosphonic acids and/or salts can be used in the practice of this invention.

Suitable dosage levels of the radioactive polyphosphonates of the present invention typically comprise about 2 to 20 milliCuries (mCi). The unique low soft tissue retention, etc., can allow even higher levels. Preferably the compound (or composition comprising two or more compounds) is prepared from high activity $PCl_3$ and care is taken to assure that all or a high proportion of the polyphosphonate be tagged in order to minimize the total dosage of polyphosphonate required to administer the desired radioactive dose. Also, the phosphonate is preferably used shortly (e.g., within three days) after preparation. A specific activity of at least about 0.01 mCi/mg of phosphonate at the time of administration is preferable. Excessive total doses of polyphosphonates, it is believed, can result in a saturation of the region of the active tumor and an "overflow" of the polyphosphonate (without regard to its level of tagging) to non-tumerous areas.

Both for storage and use, it is preferred that the compounds of this invention be in dilute, sterile, pyrogen free, aqueous solution unit dosage form. e.g., about 2 mg/ml. Such a solution reduces the probability of self degradation of the phosphonates due to the radiation given off therefrom and is suitable for direct injection to the patent, preferably intravenously. Such solutions can be further diluted if desired. Suitable glass vials with radiation resistant plastic or rubber seals are preferably used to package the solutions.

The following Examples are illustrative of the present invention:

EXAMPLE 1

A Standard Poodle with an advanced bone tumor in the left ulna was administered four injections (one per day on successive days) of a $^{32}P$-tagged disodium ethane-1-hydroxy-1,1-diphosphonate solution in the cephalic vein.

The solution was prepared by a reaction of the type described in the aforementioned U.S. Pat. No. 3,400,149 and in JACS, Vol. 49, pp. 6119, et seq. Specifically, $PCl_3$ (0.80 ml, 4 mM, 37 mCi) and 0.60 ml of glacial acetic acid were gently mixed at room temperature. The acetic acid served both as a reactant and a solvent. 0.3 ml of water was then added dropwise over a three minute period. The mixture temperature was slowly heated (over two hours) to 145°C and held at this temperature for four hours. 8 ml of water was then added to the reaction flask along with a mixing chip (Hengar granule) and the solution was refluxed for 40 hours at 145°C. resulting in a product consisting primarily of ethane-1-hydroxy-1,1-diphosphonic acid. The acid solution was adjusted to a pH of about 5 with NaOH resulting in disodium ethane-1-hydroxy-1,1-diphosphonate. Water was added to adjust the concentration to 12.9 ml of $H_2O$/mM of phosphonate and formula 3A anhydrous ethanol was added (2.5 parts ethanol/part phosphonate solution) slowly with vigorous solution to precipitate the diphosphonate. The precipitate was vacuum filtered, washed with ethanol and ethyl ether and dried. The dry product was stored in aqueous solution (50 mg/ml) in order to minimize radiation decomposition.

About 0.3 mCi per injection was used for a total of 1.2 mCi. A noticeable reduction in pain (as evidenced by, inter alia, increased activity) resulted. There were no noticeable signs of radiation sickness. Because of the advanced state of the tumor when therapy commenced and the low dosages of radioactivity administered therapy was incomplete and amputation was ultimately indicated.

EXAMPLE 2

A Great Dane with an advanced osteogenic sarcoma in the left radius was treated as in Example 1 but with five doses of 0.5 mCi each on successive days. About 10 days after the final administration of the radioactive drug, pain reduction and increased activity were noticed. No radiation sickness was noticed. Again, the tumor was in such an advanced stage when the dog became available for therapy that the therapy was only partially successful and euthanasia was ultimately indicated. A post-mortem was conducted; the tumorous bone was found to have 40 times (on a mCi/gm basis) as much radioactivity as the contralateral bone. In addition, gross pathological observation suggested that lysis (dissolution of the tumor) had occurred to some extent.

EXAMPLE 3

A Vizsla with a bone tumor in the right proximal humerus was treated as in Example 1 except that about 1 mCi was administered on each of four successive days. About 4 days after the last injection the dog progressed to the point of running using the leg which it previously had "carried".

EXAMPLE 4

A 70 kilogram adult with a bone tumor is administered intravenously disodium-ethane-1-hydroxy-1,1-diphosphonate having $^{32}P$ incorporated therein (80 mCi/gm) in five doses of 2mCi each on successive days. About 4 days after the last injection, a noticeable reduction in bone pain is observed.

Dichloromethanediphosphonic acid; tris(phosphonomethyl)-amine; methane cyclohexylhydroxydiphosphonic acid; 3,3,4,4,5,5-hexafluoro-1,2-diphosphonocyclopent-1-ene; cyclic tetraphosphonic acid; ethane-1,2 dicarboxy-1-phosphonic acid; and ethane-1,2-dicarboxy-1-phosphonic acid having incorporated therein $^{32}P$ are substituted for the ethane-1-hydroxy-1,1-diphosphonic acid and similar results are obtained.

The radioactive phosphonates herein enumerated also are suited for combined therapy with chemotherapeutic drugs. Such drugs can be conveniently classified in the following groups: alkylating agents, antimetabolites antibiotics, vinca alkaloids, hormones, enzymes (e.g., 1-asparginase) hydroxyurea and procarbazine (N-isopropyl-α-(2-methylhydrazino-p-toluamide monohydrochloride). In combined therapy using radioactive phosphonates and chemotherapeutic agents the polyphosphonate will be administered first and the other chemotherapeutic agent will be administered in conventional doses (i.e., doses on the order of those used for such chemotherapeutic agents alone) beginning at from about 1 to about 20 days after the administration of the radioactive phosphonates. This approach takes advantage of the fact that chemotherapeutic agents work during the active cycle of cells ($G_1$, S, $G_2$, M) and that radioactivity can stimulate transition of cells from the resting ($G_o$) state into the active cell cycle.

Alkylating agents suitable for use in combined therapy with radioactive phosphonates include mechlorethamine hydrochloride, (2,2'-dichloro-N-methyldietylamine hydrochloride), triethylenemelamine (2,4,6-tris(1-aziridinyl)-s-triazine), thiotepa triethylenethiophosphoroamide, bulsulfan (1,4-bis(methanesulfonoxy)butane), chlorambucil (4- p-[bis(2-chloroethyl)amino]phenyl butyric acid), cyclophosphamide(1-bis(2-chloromethyl)amino-1-oxy-2-aza-5-oxaphosphoridin), melphalan (p-(di-2-chloroethylamino)-phenylalanine) and BCNU (1,3-bis(2-chloroethyl)-1-nitrosourea).

Antimetabolites suitable for use in combined therapy with radioactive phosphonates include 6-mercaptopurine, (6-purinethiol), DON (6-diazo-5-oxo-L-norleucine), azaserine (o-diazoacetyl-L-serine), methotrexate (4-amino-$N^{10}$-methyl-pteroylglutamic acid), 5-fluorouracil, cytarabine (1-β-D-arabinofuranosylcytosine). Suitable antibiotics include actinomycin D dactinomycin, mithramycin, daunomycin and mitomycin C. Suitable vinca alkaloids include vinblastine sulfate and vincristine sulfate. The above chemotherapeutic agents and typical dosages therefore are described more fully in the Encyclopedia of Chemical Technology, 2nd Ed.(Interscience, 1971).

EXAMPLE 5

An 70 kilogram adult with a bone tumor is administered intravenously disodium-ethane-1-hydroxy-1,1-diphosphonate having $^{32}P$ incorporated therein (80 mCi/gm) in five doses of 2 mCi each on successive days. Five days after the final injection, administration of 5-fluorouracil at 15 mg/kg/day for five days is begun. An increased effectiveness over results produced with either treatment alone results and essentially no side effects beyond those normally associated with the 5-fluorouracil are observed.

EXAMPLES 6–10

When in Examples 1-5 the radionuclide $^{33}P$ is used instead of $^{32}P$ substantially the same or similar results are obtained.

Similar results are obtained by administering other chemotherapeutic agents at their conventional dosages following the administration of the radioactive phosphonates by one to as many as about 28 days thereafter.

It is apparent that the present invention provides a whole new group of compounds and methods for the treatment of calcific tumors. The foregoing examples are illustrative only and the scope of the invention is defined in the appended claims.

What is claimed is:

1. A sterile dilute composition in unit dosage form comprising from about 2 to 20 millicuries of a $^{32}P$ or $^{33}P$ tagged polyphosphonate compound suitable for the treatment of calcific tumors selected from the group consisting of:

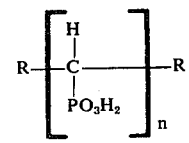

wherein each R is hydrogen or $CH_2OH$ and n is an integer of from 3 to 10;

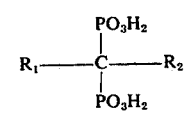

wherein $R_1$ is hydrogen, alkyl containing from 1 to about 20 carbon atoms, alkenyl containing from 2 to about 20 carbon atoms, aryl, phenylethenyl, benzyl, halogen, hydroxyl, amino, substituted amino, $-CH_2COOH$, $-CH_2PO_3H_2$, $-CH(PO_3H_2)$ (OH), or $-CH_2C(PO_3H_2)_{2n}-H$ where $n$ is 1 to 15, $R_2$ is hydrogen, lower alkyl, amino benzyl, halogen, hydroxyl, —CH$_2$COOH, —CH$_2$PO$_3$H$_2$, or —CH$_2$Ch$_2$PO$_3$H$_2$;

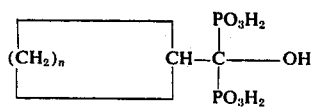 III.

wherein n is an integer of from 3 to 9;

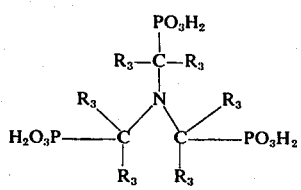 IV.

wherein each R$_3$ is hydrogen or lower alkyl (e.g., methyl, ethyl, propyl and butyl);

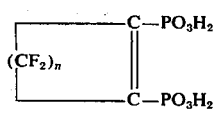 V.

wherein n is an integer of from 2 to 4;

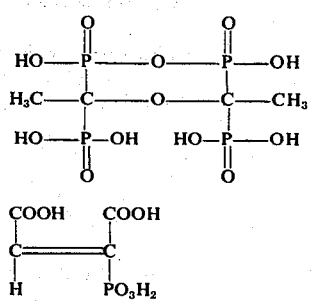 VI.

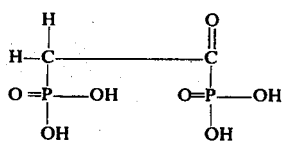 VII.

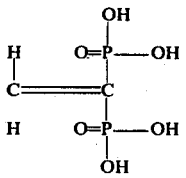 VIII.

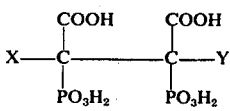 IX.

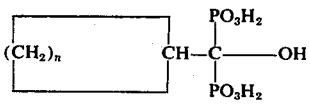 X.

wherein X and Y are each hydrogen or hydroxy; and the pharmaceutically acceptable salts of each of the foregoing acids.

2. The composition of Claim 1 wherein the polyphosphonate is ethane-1-hydroxy-1,1-diphosphonic acid or a pharmaceutically acceptable salt thereof.

3. The composition of Claim 1 wherein the polyphosphonate is dichloromethanediphosphonic acid or a pharmaceutically acceptable salt.

4. The composition of claim 1 wherein the polyphosphonate is tris (phosphonomethyl)amine or a pharmaceutically acceptable salt thereof.

5. The composition of claim 1 wherein the polyphosphonate is methanecyclohexylhydroxydiphosphonic acid or a pharmaceutically acceptable salt thereof.

6. The composition of claim 1 wherein the polyphosphonate is 3,3,4,4,5,5-hexafluoro-1,2-diphosphonocyclopent-1-ene or a pharmaceutically acceptable salt thereof.

7. The composition of claim 1 wherein the polyphosphonate is cyclic tetraphosphonic acid or a pharmaceutically acceptable salt thereof.

8. The composition of claim 1 wherein the polyphosphonate is ethene-1,2-dicarboxy-1-phosphonic acid or a pharmaceutically acceptable salt thereof.

9. The composition of claim 1 wherein the polyphosphonate is ethane-1,2-dicarboxy-1,2-diphosphonic acid or a pharmaceutically acceptable salt thereof.

10. A method for the treatment of calcific tumors comprising systemically administering to an animal afflicted therewith a safe but effective dose of a radioactive compound tagged with $^{32}$P or $^{33}$P selected from the group consisting of:

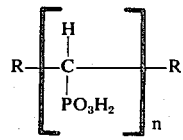 I.

wherein each R is hydrogen or CH$_2$OH or CH$_2$OH and n is an integer of from 3 to 10,

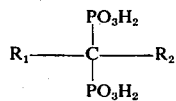 II.

wherein R$_1$ is hydrogen, alkyl containing from 1 to about 20 carbon atoms, alkenyl containing from 2 to about 20 carbon atoms, aryl, phenylethenyl, benzyl, halogen, hydroxyl, amino, substituted amino, —CH$_2$COOH, —CH$_2$PO$_3$H$_2$, -CH(PO$_3$H$_2$) (OH), or —[CH$_2$C(PO$_3$H$_2$)$_n$-H, where n is 1 to 15, R$_2$ is hydrogen, lower alkyl, amino, benzyl, halogen, hydroxyl, —CH$_2$COOH, —CH$_2$PO$_3$H$_2$, or —CH$_2$Ch$_2$PO$_3$H$_2$;

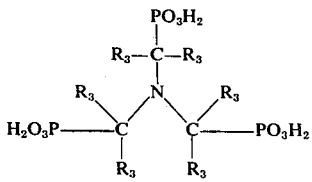 III.

wherein n is an integer of from 3 to 9,

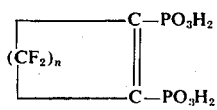 IV.

wherein each R$_3$ is hydrogen or lower alkyl (e.g., methyl, ethyl, propyl and butyl);

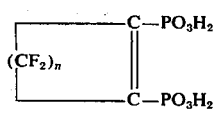 V.

wherein n is an integer of from 2 to 4;

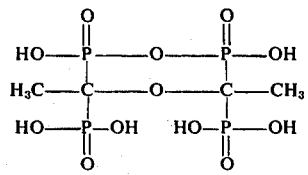   VI.

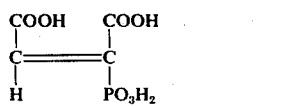   VII.

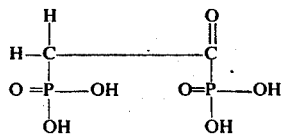   VIII.

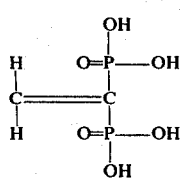   IX.

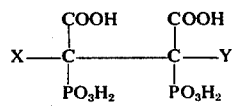   X.

wherein X and Y are each hydrogen or hydroxy; and the pharmaceutically acceptable salts thereof.

11. The method of claim 10 wherein said compound is ethane-1-hydroxy-1,1-diphosphonic acid or a pharmaceutically acceptable salt thereof.

12. The method of claim 10 wherein said compound is dichloromethanediphosphonic acid or a pharmaceutically acceptable salt thereof.

13. A method for the treatment of calcific tumors comprising systemically administering to an animal affected therewith a safe but effective dose of a radioactive compound tagged with $^{32}P$ or $^{33}P$ selected from the group consisting of:

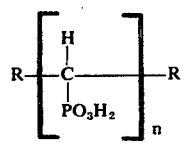   I.

wherein each R is hydrogen or CH$_2$OH and n is an integer of from 3 to 10;

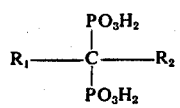   II.

wherein $R_1$ is hydrogen, alkyl containing from 1 to about 20 carbon atoms, alkenyl containing from 2 to about 20 carbon atoms, aryl, phenylethenyl, benzyl, halogen, hydroxyl, amino, substituted amino, —CH$_2$COOH, —CH$_2$COOH, —CH$_2$PO$_3$H$_2$, —CH(PO$_3$H$_2$)(OH), or -[CH$_2$C(PO$_3$H$_2$)$_2$]$_n$-H, where n is 1 to 15, $R_2$ is hydrogen, lower alkyl, amino, benzyl, halogen, hydroxyl, —CH$_2$COOH, —CH$_2$PO$_3$H$_2$, or CH$_2$CH$_2$PO$_3$H$_2$;

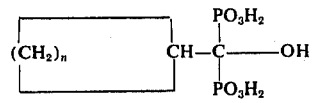   III.

wherein *n* is an integer of from 3 to 9;

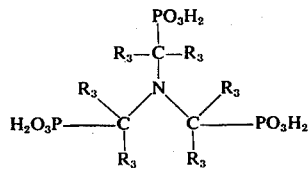   IV.

wherein each $R_3$ is hydrogen or lower alkyl (e.g., methyl, ethyl, propyl and butyl);

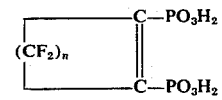   V.

wherein *n* is an integer of from 2 to 4;

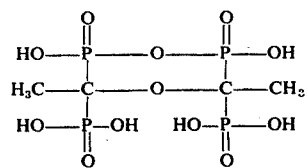   VI.

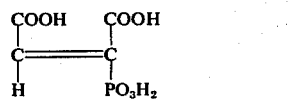   VII.

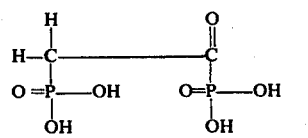   VIII.

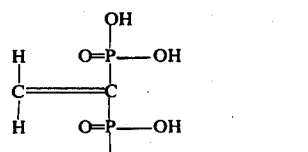   IX.

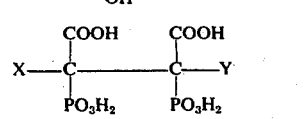   X.

wherein X and Y are each hydrogen or hydroxy; and the pharmaceutically acceptable salts thereof; and subsequently administering a chemotherapeutic agent selected from the group consisting of: alkylating agents; antimetabolites; antibiotics; vinca alkaloids; hormones; enzymes; hydroxyurea; and procabazine.

14. The method of claim 13 wherein said compound is ethane-1-hydroxy-1,1-diphosphonic acid or a pharmaceutically acceptable salt thereof.

15. The method of claim 13 wherein said compound is dichloromethanediphosphonic acid or a pharmaceutically acceptable salt thereof.

* * * * *